(12) United States Patent
Lawrence et al.

(10) Patent No.: US 10,531,823 B2
(45) Date of Patent: Jan. 14, 2020

(54) SYSTEMS AND METHODS FOR GENERATING NOTIFICATIONS BASED ON BLADDER VOLUME SIGNALS AND BLADDER MUSCLE SIGNALS

(71) Applicant: Hill-Rom Services, Inc., Batesville, IN (US)

(72) Inventors: Brian L. Lawrence, Cincinnati, OH (US); Eric D. Agdeppa, Cincinnati, OH (US); Michael S. Hood, Batesville, IN (US); Yongji Fu, Harrison, OH (US)

(73) Assignee: HILL-ROM SERVICES, INC., Batesville, IN (US)

( * ) Notice: Subject to any disclaimer, the term of this patent is extended or adjusted under 35 U.S.C. 154(b) by 0 days.

(21) Appl. No.: 15/601,390

(22) Filed: May 22, 2017

(65) Prior Publication Data

US 2017/0340259 A1  Nov. 30, 2017

Related U.S. Application Data

(60) Provisional application No. 62/340,814, filed on May 24, 2016.

(51) Int. Cl.
*A61B 5/20* (2006.01)
*A61B 5/11* (2006.01)
(Continued)

(52) U.S. Cl.
CPC .......... *A61B 5/202* (2013.01); *A61B 5/04882* (2013.01); *A61B 5/1115* (2013.01);
(Continued)

(58) Field of Classification Search
None
See application file for complete search history.

(56) References Cited

U.S. PATENT DOCUMENTS 5,103,835 A * 4/1992 Yamada ............... A61B 5/202
600/547
8,287,452 B2  10/2012 Young et al.
(Continued)

FOREIGN PATENT DOCUMENTS

EP       1702587 A1    9/2006
WO    2007035887 A2    3/2007
(Continued)

OTHER PUBLICATIONS

T Schlebusch et al., "Bladder volume estimation from electrical impedance tomography", 2014, Physiol. Meas. 35 1813-1815.*
(Continued)

*Primary Examiner* — Christopher Koharski
*Assistant Examiner* — James Moss
(74) *Attorney, Agent, or Firm* — Dinsmore & Shohl LLP (57) ABSTRACT

Systems and methods for generating notifications based on bladder volume signals and bladder muscle signals are disclosed. A system includes a processor, a plurality of bladder electrical signal application electrodes, a plurality of bladder volume measurement electrodes, a plurality of bladder muscle measurement electrodes, a memory module communicatively coupled to the processor, and machine readable instructions stored in the memory module. When executed by the processor, the machine readable instructions cause the system to output a first electrical output signal with the plurality of bladder electrical signal application electrodes, receive the bladder volume signal at the plurality of bladder volume measurement electrodes in response to the first electrical output signal, receive the bladder muscle signal at the plurality of bladder muscle measurement electrodes, and generate the notification based on the bladder volume signal and the bladder muscle signal.

14 Claims, 4 Drawing Sheets

(51) Int. Cl.
*A61B 5/0488* (2006.01)
*A61B 5/00* (2006.01)

(52) U.S. Cl.
CPC ............ *A61B 5/204* (2013.01); *A61B 5/6874* (2013.01); *A61B 5/746* (2013.01)

(56) References Cited

U.S. PATENT DOCUMENTS

| | | | | |
|---|---|---|---|---|
| 2002/0062060 A1* | 5/2002 | Gross | ............... | A61N 1/36007 600/30 |
| 2005/0038328 A1* | 2/2005 | Stoehrer | ............ | A61B 5/02055 600/301 |
| 2007/0100387 A1* | 5/2007 | Gerber | ................... | A61B 5/053 607/41 |
| 2010/0292603 A1 | 11/2010 | Shiffman et al. | | |
| 2011/0224665 A1 | 9/2011 | Crosby et al. | | |
| 2012/0035496 A1 | 2/2012 | Denison et al. | | |
| 2012/0245436 A1* | 9/2012 | Rutkove | .............. | A61B 5/4519 600/301 |
| 2012/0323136 A1 | 12/2012 | Shiffman et al. | | |
| 2013/0035606 A1 | 2/2013 | Wichner | | |
| 2013/0041283 A1 | 2/2013 | Wichner | | |
| 2013/0060304 A1 | 3/2013 | LaTendresse et al. | | |
| 2013/0338473 A1 | 12/2013 | Bohorquez et al. | | |
| 2014/0039341 A1 | 2/2014 | Bohorquez et al. | | |
| 2014/0194949 A1 | 7/2014 | Wichner | | |
| 2017/0095670 A1* | 4/2017 | Ghaffari | ............... | A61B 5/0024 |

FOREIGN PATENT DOCUMENTS

| | | |
|---|---|---|
| WO | 2010136924 A1 | 12/2010 |
| WO | 2011022068 A1 | 2/2011 |
| WO | 2011112773 A2 | 9/2011 |
| WO | 2012149471 A2 | 11/2012 |
| WO | 2013013782 A2 | 1/2013 |
| WO | 2014058793 A1 | 4/2014 |
| WO | 2014062925 A1 | 4/2014 |
| WO | 2014071150 A1 | 5/2014 |
| WO | 2014107624 A1 | 7/2014 |

OTHER PUBLICATIONS

Anne B. Chin et al., "Optimizing Measurement of the Electrical Anisotropy of Muscle", Muscle Nerve. May 2008 ; 37(5): 560-565. doi:10.1002/mus.20981.*

Cromwell, Marlena and Melda Hardison. Handbook of Electronic & Analogue Circuits. vol. 1st ed, College Publishing House, 2012.*

Ruesch et al, The Relation Between Electromyographic Measurement and Subjective Reports of Muscular Relaxation, Psychosomatic Medicine, 1943, vol. 5, 132-138.

Tarulli et al, Electrical impedance myography in the bedside assessment of inflammatory myopathy, Neurology, 2005, 451-452.

Gill et al, Feasibility of Fluid Volume Conductance to Assess Bladder Volume, Wiley-Liss, Inc., Neurourology and Urodynamics, 2008, 525-531.

Liao et al, Noninvasive electrical impedance analysis to measure human urinary bladder volume, Journal of Obstetrics and Gynaecology Research, 2011, vol. 37 No. 8, 1071-1075, Taiwan.

Garmirian et al, Discriminating Neurogenic From Myopathic Disease via Measurement of Muscle Anisotropy, Mucle Nerve, 2009.

* cited by examiner

SYSTEMS AND METHODS FOR GENERATING NOTIFICATIONS BASED ON BLADDER VOLUME SIGNALS AND BLADDER MUSCLE SIGNALS

CROSS REFERENCE TO RELATED APPLICATIONS

This application claims the benefit of U.S. Provisional Application No. 62/340,814, entitled "SYSTEMS AND METHODS FOR GENERATING NOTIFICATIONS BASED ON BLADDER VOLUME SIGNALS AND BLADDER MUSCLE SIGNALS," filed May 24, 2016, the entirety of which is hereby incorporated by reference.

TECHNICAL FIELD

The present specification generally relates to systems and methods for providing notifications and, more specifically, to systems and methods for generating notifications based on bladder volume signals and bladder muscle signals.

BACKGROUND

Patients in hospitals and other care settings may spend a substantial amount of time in beds. It may be difficult or unsafe for some patients to exit the beds without assistance in order to perform a variety of activities. For example, it may be unsafe due to a risk of fall or injury for some patients to exit the bed without assistance when the patient has an urge to urinate. It may be desirable to generate a notification that the patient may need to exit the bed to urinate before the patient does so without assistance.

Accordingly, a need exists for systems and methods for generating notifications based on bladder volume signals and bladder muscle signals.

SUMMARY

In one embodiment, a system for generating a notification based on a bladder volume signal and a bladder muscle signal includes a processor, a plurality of bladder electrical signal application electrodes communicatively coupled to the processor, a plurality of bladder volume measurement electrodes communicatively coupled to the processor, a plurality of bladder muscle measurement electrodes communicatively coupled to the processor, a memory module communicatively coupled to the processor, and machine readable instructions stored in the memory module. When executed by the processor, the machine readable instructions cause the system to output a first electrical output signal with the plurality of bladder electrical signal application electrodes, receive the bladder volume signal at the plurality of bladder volume measurement electrodes in response to the first electrical output signal, receive the bladder muscle signal at the plurality of bladder muscle measurement electrodes, and generate the notification based on the bladder volume signal and the bladder muscle signal.

In another embodiment, a system for generating a notification based on a comparison of a current bladder void parameter and a bladder void parameter threshold includes a processor, a plurality of bladder electrical signal application electrodes communicatively coupled to the processor, a plurality of bladder volume measurement electrodes communicatively coupled to the processor, a memory module communicatively coupled to the processor, and machine readable instructions stored in the memory module. When executed by the processor, the machine readable instructions cause the system to output a first electrical output signal with the plurality of bladder electrical signal application electrodes, receive a bladder volume signal at the plurality of bladder volume measurement electrodes in response to the first electrical output signal, determine a first bladder void event based on the received bladder volume signal, and determine a first bladder void parameter associated with the first bladder void event. The first bladder void parameter is determined based on the bladder volume signal. When executed by the processor, the machine readable instructions further cause the system to determine a second bladder void event based on the received bladder volume signal, and determine a second bladder void parameter associated with the second bladder void event. The second bladder void parameter is determined based on the bladder volume signal. When executed by the processor, the machine readable instructions further cause the system to determine a first bladder void parameter threshold based on the first bladder void parameter and the second bladder void parameter, determine a first current bladder void parameter based on the bladder volume signal, compare the first current bladder void parameter to the first bladder void parameter threshold, and generate a notification based on the comparison of the first current bladder void parameter and the first bladder void parameter threshold.

In yet another embodiment, a system for generating a notification based on a bladder volume signal and a bladder muscle signal includes a processor, a plurality of bladder electrical signal application electrodes communicatively coupled to the processor, a plurality of bladder volume measurement electrodes communicatively coupled to the processor, a plurality of bladder muscle electrical signal application electrodes communicatively coupled to the processor, a plurality of bladder muscle measurement electrodes communicatively coupled to the processor, network interface hardware communicatively coupled to the processor, a memory module communicatively coupled to the processor, and machine readable instructions stored in the memory module. When executed by the processor, the machine readable instructions cause the system to output a first electrical output signal with the plurality of bladder electrical signal application electrodes, receive the bladder volume signal at the plurality of bladder volume measurement electrodes in response to the first electrical output signal, output a second electrical output signal with the plurality of bladder muscle electrical signal application electrodes, receive the bladder muscle signal at the plurality of bladder muscle measurement electrodes in response to the second electrical output signal, generate the notification based on the bladder volume signal and the bladder muscle signal, and transmit the notification to a portable electronic device.

These and additional features provided by the embodiments of the present disclosure will be more fully understood in view of the following detailed description, in conjunction with the drawings.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

Figure 1:
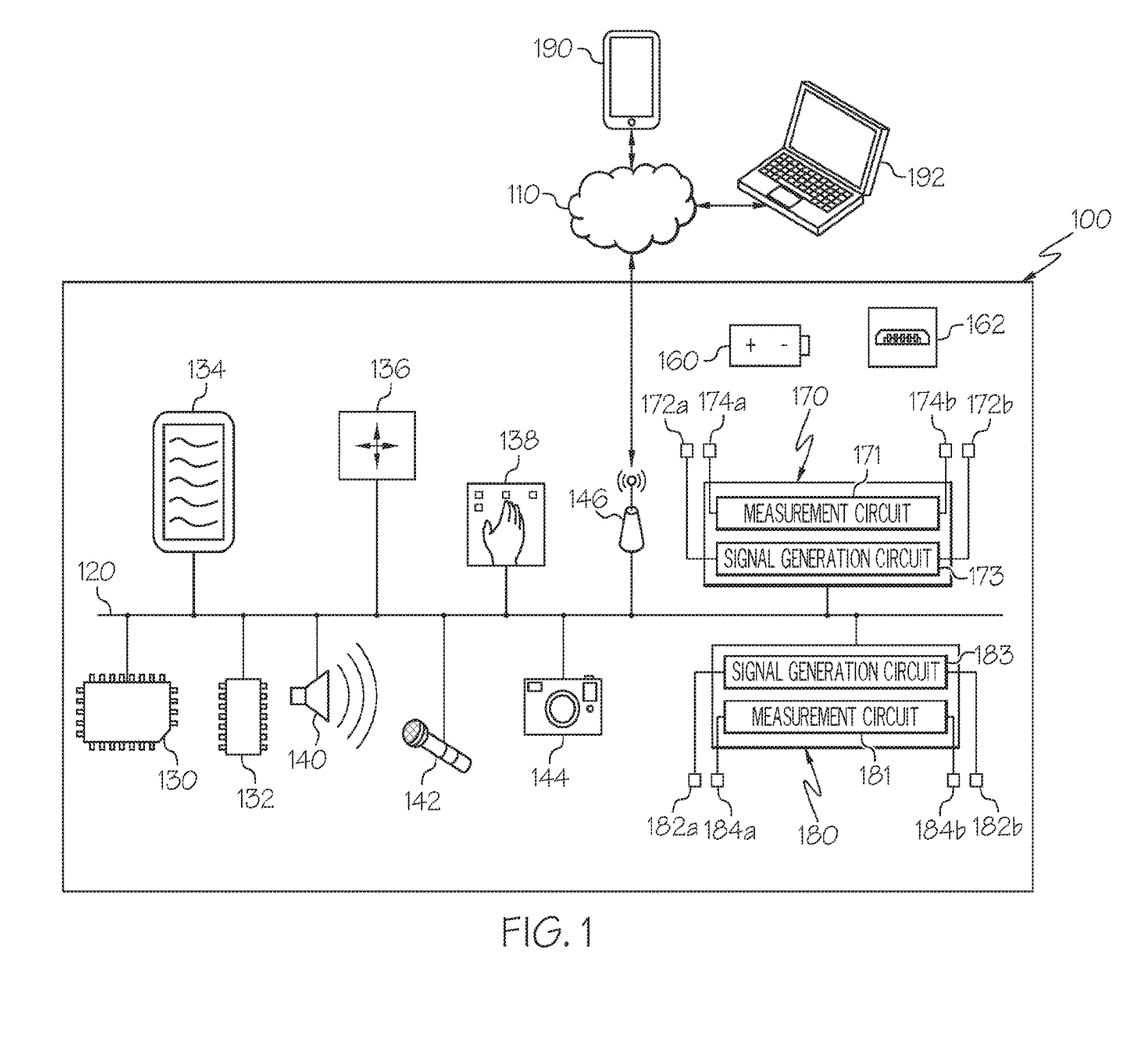
FIG. 1 schematically depicts a system including a number of electrodes, sensors, and electronic components, according to one or more embodiments shown and described herein.

The embodiments disclosed herein include systems and methods for generating notifications based on bladder volume signals and bladder muscle signals. Systems and methods for generating notifications based on a comparison of a current bladder void parameter and a bladder void parameter threshold are also disclosed. Referring generally to FIG. 1, a system includes a plurality of bladder electrical signal application electrodes communicatively coupled to the processor, a plurality of bladder volume measurement electrodes communicatively coupled to the processor, and a plurality of bladder muscle measurement electrodes communicatively coupled to the processor. The system outputs a first electrical output signal with the plurality of bladder electrical signal application electrodes, receives the bladder volume signal at the plurality of bladder volume measurement electrodes in response to the first electrical output signal, receives the bladder muscle signal at the plurality of bladder muscle measurement electrodes, and generates the notification based on the bladder volume signal and the bladder muscle signal. By generating a notification (e.g., a notification indicative of a predicted bed exit, a predicted need for a person to urinate, or the like) based on both of the bladder volume signal and the bladder muscle signal, reliability of the notification may be increased as compared to a system that utilizes only one of the bladder muscle signal and the bladder volume signal since a system that only utilizes one signal could result in the generation of false notifications. The various systems and methods for generating notifications based on bladder volume signals and bladder muscle signals and systems and methods for generating notifications based on a comparison of a current bladder void parameter and a bladder void parameter threshold will be described in more detail herein with specific reference to the corresponding drawings.

Referring now to FIG. 1, one embodiment of a system 100 is schematically depicted. The system 100 includes a communication path 120, one or more processors 130, one or more memory modules 132, one or more displays 134, one or more inertial measurement units 136, tactile input hardware 138, one or more speakers 140, one or more microphones 142, one or more cameras 144, network interface hardware 146, one or more power sources 160, one or more charging ports 162, a bladder volume measurement unit 170, and a bladder muscle measurement unit 180. The various components of the system 100 and the interaction thereof will be described in detail below.

Still referring to FIG. 1, the communication path 120 may be formed from any medium that is capable of transmitting a signal such as, for example, conductive wires, conductive traces, optical waveguides, or the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a bus. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium. The communication path 120 communicatively couples the various components of the system 100. As used herein, the term "communicatively coupled" means that coupled components are capable of exchanging data signals with one another such as, for example, electrical signals via conductive medium, electromagnetic signals via air, optical signals via optical waveguides, and the like.

Each of the one or more processors 130 of the system 100 may be any device capable of executing machine readable instructions. Accordingly, each of the one or more processors 130 may be a controller, an integrated circuit, a microchip, a computer, or any other computing device. Each of the one or more processors 130 is communicatively coupled to the other components of the system 100 by the communication path 120. Accordingly, the communication path 120 may communicatively couple any number of processors with one another, and allow the components coupled to the communication path 120 to operate in a distributed computing environment. Specifically, each of the components may operate as a node that may send and/or receive data.

Each of the one or more memory modules 132 of the system 100 is coupled to the communication path 120 and communicatively coupled to the one or more processors 130. Each of the one or more memory modules 132 may comprise RAM, ROM, flash memories, hard drives, or any device capable of storing machine readable instructions such that the machine readable instructions can be accessed and executed by the one or more processors 130. The machine readable instructions may comprise logic or algorithm(s) written in any programming language of any generation (e.g., 1GL, 2GL, 3GL, 4GL, or 5GL) such as, for example, machine language that may be directly executed by the one or more processors 130, or assembly language, object-oriented programming (OOP), scripting languages, microcode, etc., that may be compiled or assembled into machine readable instructions and stored in the one or more memory modules 132. Alternatively, the machine readable instructions may be written in a hardware description language (HDL), such as logic implemented via either a field-programmable gate array (FPGA) configuration or an application-specific integrated circuit (ASIC), or their equivalents. Accordingly, the functionality described herein may be implemented in any conventional computer programming language, as pre-programmed hardware elements, or as a combination of hardware and software components.

Each of the one or more displays 134 is coupled to the communication path 120 and communicatively coupled to the one or more processors 130. Each of the one or more displays 134 may be any device capable of providing visual output. Each of the one or more displays 134 may include any medium capable of transmitting an optical output such as, for example, a cathode ray tube, light emitting diodes, a liquid crystal display, a plasma display, or the like. In some embodiments, the one or more displays 134 may include a touchscreen that, in addition to providing optical information, detects the presence and location of a tactile input upon a surface of or adjacent to the display. In such embodiments, the touchscreen may receive mechanical input directly upon the optical output provided by the display. In some embodiments, the one or more displays 134 includes a three dimensional tactile display including a surface, portions of which may raise to communicate information. Additionally, it is noted that each of the one or more displays 134 can include at least one processor or memory module. Some embodiments of the system 100 may not include the one or more displays 134.

Each of the one or more inertial measurement units 136 is coupled to the communication path 120 and communicatively coupled to the one or more processors 130. Each of the one or more inertial measurement units 136 may include one or more accelerometers and one or more gyroscopes. Each of the one or more inertial measurement units 136 transforms sensed physical movement of the system 100 into a signal indicative of an orientation, a rotation, a velocity, or an acceleration of the system 100. Some embodiments of the system 100 may not include the one or more inertial measurement units 136, such as embodiments that include an accelerometer but not a gyroscope, embodiments that include a gyroscope but not an accelerometer, or embodiments that include neither an accelerometer nor a gyroscope. Some embodiments may not include an accelerometer or a gyroscope.

Still referring to FIG. 1, the tactile input hardware 138 is coupled to the communication path 120 and communicatively coupled to the one or more processors 130. The tactile input hardware 138 may be any device capable of transforming mechanical pressure (e.g, the pressure from a user contacting the tactile input hardware 138) into a data signal that can be transmitted over the communication path 120 such as, for example, a button, a switch, a knob, a microphone or the like. In some embodiments, the tactile input hardware 138 includes a power button, a volume button, an activation button, a scroll button, or the like. In some embodiments, the tactile input hardware 138 includes a pressure sensor, a touch strip, a pressure strip, or the like. Some embodiments may not include the tactile input hardware 138.

Each of the one or more speakers 140 is coupled to the communication path 120 and communicatively coupled to the one or more processors 130. Each of the one or more speakers 140 transforms data signals from the system 100 into audible mechanical vibrations. However, it should be understood that in other embodiments the system 100 may not include the one or more speakers 140.

Each of the one or more microphones 142 is coupled to the communication path 120 and communicatively coupled to the one or more processors 130. Each of the one or more microphones 142 may be any device capable of transforming a mechanical vibration associated with sound into an electrical signal indicative of the sound. Some embodiments may not include the one or more microphones 142.

Each of the one or more cameras 144 is coupled to the communication path 120 and communicatively coupled to the one or more processors 130. Each of the one or more cameras 144 may be any device having an array of sensing devices (e.g., pixels) capable of detecting radiation in an ultraviolet wavelength band, a visible light wavelength band, or an infrared wavelength band. Each of the one or more cameras 144 may have any resolution. The one or more cameras 144 may include an omni-directional camera, or a panoramic camera. In some embodiments, one or more optical components, such as a mirror, fish-eye lens, or any other type of lens may be optically coupled to at least one of the one or more cameras 144. Some embodiments may not include the one or more cameras 144.

The network interface hardware 146 is coupled to the communication path 120 and communicatively coupled to the one or more processors 130. The network interface hardware 146 may be any device capable of transmitting and/or receiving data via a network 110. Accordingly, the network interface hardware 146 can include a communication transceiver for sending and/or receiving any wired or wireless communication. For example, the network interface hardware 146 may include an antenna, a modem, LAN port, Wi-Fi card, WiMax card, mobile communications hardware, near-field communication hardware, satellite communication hardware and/or any wired or wireless hardware for communicating with other networks and/or devices. In some embodiments, the network interface hardware 146 includes hardware configured to operate in accordance with the BLUETOOTH wireless communication protocol. In some embodiments, the network interface hardware 146 may include a BLUETOOTH send/receive module for sending and receiving BLUETOOTH communications to/from a portable electronic device 190. Some embodiments may not include the network interface hardware 146.

The system 100 is powered by the one or more power sources 160, each of which is electrically coupled to the various electrical components of the system 100. Each of the one or more power sources 160 may be any device capable of providing energy for user by the system 100. In some embodiments, the one or more power sources 160 may include a power supply that transforms electrical power provided from a wall outlet to electrical energy used to power the system 100. In some embodiments, the one or more power sources 160 include one or more batteries for storing electric energy for later use by the system 100. In some embodiments, the one or more batteries may include a rechargeable battery, such as a lithium-ion battery or a nickel-cadmium battery. In embodiments in which the one or more batteries include a rechargeable battery, the system 100 may include the one or more charging ports 162, each of which may be used to charge the one or more batteries. Some embodiments may not include the one or more batteries, such as embodiments in which the system 100 is powered by solar energy or energy harvested from the environment. Some embodiments may not include the one or more charging ports 162, such as embodiments in which the imaging device utilizes disposable batteries for power or is powered via a wall plug.

Still referring to FIG. 1, the bladder volume measurement unit 170 includes a measurement circuit 171, a signal generation circuit 173, a plurality of bladder electrical signal application electrodes 172a, 172b, and a plurality of bladder volume measurement electrodes 174a, 174b. The bladder volume measurement unit 170 and the components thereof are coupled to the communication path 120 and communicatively coupled to the one or more processors 130. The plurality of bladder electrical signal application electrodes 172a, 172b includes a first bladder electrical signal application electrode 172a and a second bladder electrical signal application electrode 172b, which are coupled to the signal generation circuit 173, though some embodiments may only include one bladder electrical signal application electrode or more than two bladder electrical signal application electrodes. The plurality of bladder volume measurement electrodes 174a, 174b includes a first bladder volume measurement electrode 174a and a second bladder volume measurement electrode 174b, which are coupled to the measurement circuit 171. Some embodiments may only include one bladder volume measurement electrode or more than two bladder volume measurement electrodes. The measurement circuit 171 includes one or more electrical components configured to measure one or more parameters of a bladder volume signal received at the plurality of bladder volume measurement electrodes 174a, 174b. The signal generation circuit 173 includes one or more electrical components configured to output an electrical signal with the plurality of bladder electrical signal application electrodes 172a, 172b. Some embodiments may not include the signal generation circuit 173 and the plurality of bladder electrical signal application electrodes 172a, 172b, such as embodiments that measure one or more parameters of a bladder volume signal received at the plurality of bladder volume measurement electrodes 174a, 174b without first outputting a signal with the signal generation circuit 173, the response to which is measured with the measurement circuit 171. Furthermore, some embodiments may use the measurement circuit 171 and the plurality of bladder volume measurement electrodes 174a, 174b to both output an electrical signal and to receive the bladder volume signal in response to the output signal.

Still referring to FIG. 1, the bladder muscle measurement unit 180 includes a measurement circuit 181, a signal generation circuit 183, a plurality of bladder muscle electrical signal application electrodes 182a, 182b, and a plurality of bladder muscle measurement electrodes 184a, 184b. The bladder muscle measurement unit 180 and the components thereof are coupled to the communication path 120 and communicatively coupled to the one or more processors 130. The plurality of bladder muscle electrical signal application electrodes 182a, 182b includes a first bladder muscle electrical signal application electrode 182a and a second bladder muscle electrical signal application electrode 182b, which are coupled to the signal generation circuit 183, though some embodiments may only include one bladder muscle electrical signal application electrode or more than two bladder muscle electrical signal application electrodes. The plurality of bladder muscle measurement electrodes 184a, 184b includes a first bladder muscle measurement electrode 184a and a second bladder muscle measurement electrode 184b, which are coupled to the measurement circuit 181, though some embodiments may only include one bladder muscle measurement electrode or more than two bladder muscle measurement electrodes. The measurement circuit 181 includes one or more electrical components configured to measure one or more parameters of a bladder muscle signal received at the plurality of bladder muscle measurement electrodes 184a, 184b. The signal generation circuit 183 includes one or more electrical components configured to output an electrical signal with the plurality of bladder muscle electrical signal application electrodes 182a, 182b. Some embodiments may not include the signal generation circuit 183 and the plurality of bladder muscle electrical signal application electrodes 182a, 182b, such as embodiments that measure one or more parameters of a bladder muscle signal received at the plurality of bladder muscle measurement electrodes 184a, 184b without first outputting a signal with the signal generation circuit 183, the response to which is measured with the measurement circuit 181. Furthermore, some embodiments may use the measurement circuit 181 and the plurality of bladder muscle measurement electrodes 184a, 184b to both output an electrical signal and to receive the bladder muscle signal in response to the output signal.

Still referring to FIG. 1, in some embodiments, the system 100 may be communicatively coupled to a portable electronic device 190 and a remote computing device 192 via a network 110. In some embodiments, the network 110 is a personal area network that utilizes BLUETOOTH technology to communicatively couple the system 100, the portable electronic device 190 and the remote computing device 192. In other embodiments, the network 110 may include one or more computer networks (e.g., a personal area network, a local area network, or a wide area network), cellular networks, satellite networks and/or a global positioning system and combinations thereof. Accordingly, the system 100 can be communicatively coupled to the network 110 via wires, via a wide area network, via a local area network, via a personal area network, via a cellular network, via a satellite network, or the like. Suitable local area networks may include wired. Ethernet and/or wireless technologies such as, for example, wireless fidelity (Wi-Fi). Suitable personal area networks may include wireless technologies such as, for example, IrDA, BLUETOOTH, Wireless USB, Z-Wave, ZigBee, and/or other near field communication protocols. Suitable personal area networks may similarly include wired computer buses such as, for example, USB and FireWire. Suitable cellular networks include, but are not limited to, technologies such as LIE, WiMAX, UMTS, CDMA, and GSM.

As stated above, the network 110 may be utilized to communicatively couple the system 100 with the portable electronic device 190 and the remote computing device 192. Each of the portable electronic device 190 and the remote computing device 192 may be a computing device including one or more processors and one or more memory modules, and network interface hardware. In some embodiments, the portable electronic device 190 may be a portable device, such as a mobile phone, a smartphone, a personal digital assistant, a dedicated mobile media player, a mobile personal computer, a laptop computer, and/or any other portable electronic device capable of being communicatively coupled with the system 100. In some embodiments, the portable electronic device 190 may be transported by a caregiver or nurse of a patient. In some embodiments, the remote computing device 192 may be a computing system remote from the system 100, such as a computing device at a nurse station, or the like. Each of the portable electronic device 190 and the remote computing device 192 may include one or more processors and one or more memories. The one or more processors can execute logic to communicate with the system 100. The portable electronic device 190 and the remote computing device may be configured with wired and/or wireless communication functionality for communicating with the system 100. In some embodiments, the portable electronic device 190 and/or the remote computing device 192 may perform one or more elements of the functionality described herein, such as in embodiments in which the functionality described herein is distributed between the system 100, the portable electronic device 190, and/or the remote computing device 192.

Figure 2:
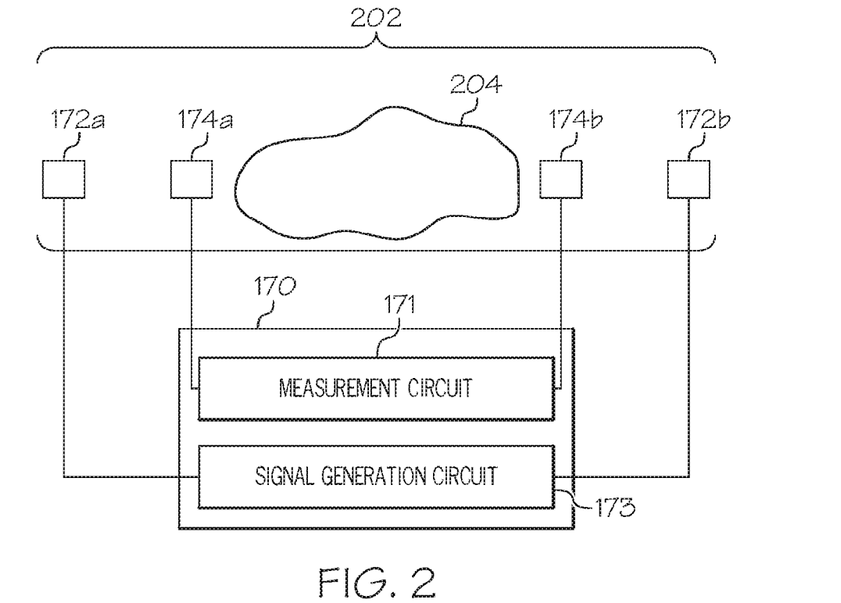
FIG. 2 schematically depicts a bladder volume measurement unit with electrodes applied to a tissue region to measure a bladder volume, according to one or more embodiments shown and described herein.

Referring now to FIG. 2, the bladder volume measurement unit 170 is shown with electrodes coupled to a tissue region 202 in order to measure a bladder volume of a bladder 204. The electrodes may be placed in a variety of locations of a patient. In some embodiments, such as what is depicted in FIG. 2, the electrodes may be applied to the skin of the patient at locations such that the bladder 204 is disposed between the first bladder electrical signal application electrode 172a and the second bladder electrical signal application electrode 172b, and such that the bladder 204 is disposed between the first bladder volume measurement electrode 174a and the second bladder volume measurement electrode 174b. A bladder volume signal is received at the plurality of bladder volume measurement electrodes 174a, 174b and processed by the measurement circuit 171 that is coupled to the plurality of bladder volume measurement electrodes. In some embodiments, the received bladder volume signal is processed in order to determine a bladder volume, as will be described in further detail below.

Still referring to FIG. 2, in some embodiments, a first electrical output signal is generated with the signal generation circuit 173 and output with the plurality of bladder electrical signal application electrodes 172a, 172b. The first electrical output signal may be an electrical signal of any type. For example, the first electrical output signal may be an alternating current signal having a constant peak-to-peak voltage, an alternating current signal having a constant current, an alternating current signal having a varying peak-to-peak voltage, an alternating current signal having a varying current, an alternating signal having a constant frequency, an alternating current signal having a varying frequency, a direct current signal having a constant voltage, a direct current signal having a constant current, a direct current signal having a varying voltage, a direct current signal having a varying current, or the like. The first electrical output signal may be a sine wave signal, a square wave signal, a triangular signal, or any other waveform. In embodiments that output the first electrical output signal, the bladder volume signal may be received at the plurality of bladder volume measurement electrodes 174a, 174b in response to the first electrical output signal. In some embodiments that output the first electrical output signal, the first electrical output signal may be an alternating current voltage signal having a first voltage and a first frequency. In some embodiments, the first frequency may be between 10 kHz and 100 kHz, though other embodiments may output signals having different frequencies.

Still referring to FIG. 2, the bladder volume signal received at the plurality of bladder volume measurement electrodes 174a, 174b may be processed to determine the bladder volume. In some embodiments, a bladder volume signal parameter of the bladder volume signal is measured. The bladder volume signal parameter may be a voltage of the bladder volume signal, a current of the bladder volume signal, a standard deviation of the bladder volume signal, a frequency of the bladder volume signal, or any other signal parameter. For example, in some embodiments, the bladder volume signal parameter is a bladder volume signal current. A bladder electrical impedance may be determined based on the bladder volume signal current, such as by calculating the bladder electrical impedance as a function of the bladder volume signal current and one or more characteristics (e.g., voltage, frequency, etc.) of the first electrical output signal. The bladder volume may be determined based on the calculated or determined electrical impedance (e.g., based on a mapping or equation that determines bladder volume from a calculated or determined bladder electrical impedance). By way of another non-limiting example, in some embodiments, the bladder volume signal parameter is a bladder volume signal voltage. A bladder electrical impedance may be determined based on the bladder volume signal voltage, such as by calculating the bladder electrical impedance as a function of the bladder volume signal voltage and one or more characteristics (e.g., current) of the first electrical output signal. The bladder volume may be determined based on the calculated or determined electrical impedance (e.g., based on a mapping or equation that determines bladder volume from a calculated or determined bladder electrical impedance).

Still referring to FIG. 2, in some embodiments that output the first electrical output signal with the plurality of bladder electrical signal application electrodes 172a, 172b, the first electrical output signal may be a constant current signal and the bladder volume may be determined based on a measured voltage of the bladder volume signal received at the plurality of bladder volume measurement electrodes 174a, 174b, such as by calculating an impedance based on the measured voltage, and determining the bladder volume based on the calculated impedance. In some embodiments that output the first electrical output signal with the plurality of bladder electrical signal application electrodes 172a, 172b, the first electrical output signal may be a constant voltage signal and bladder volume may be determined based on a measured current of the bladder volume signal received at the plurality of bladder volume measurement electrodes 174a, 174b, such as by calculating an impedance based on the measured current, and determining the bladder volume based on the calculated impedance.

Figure 3:
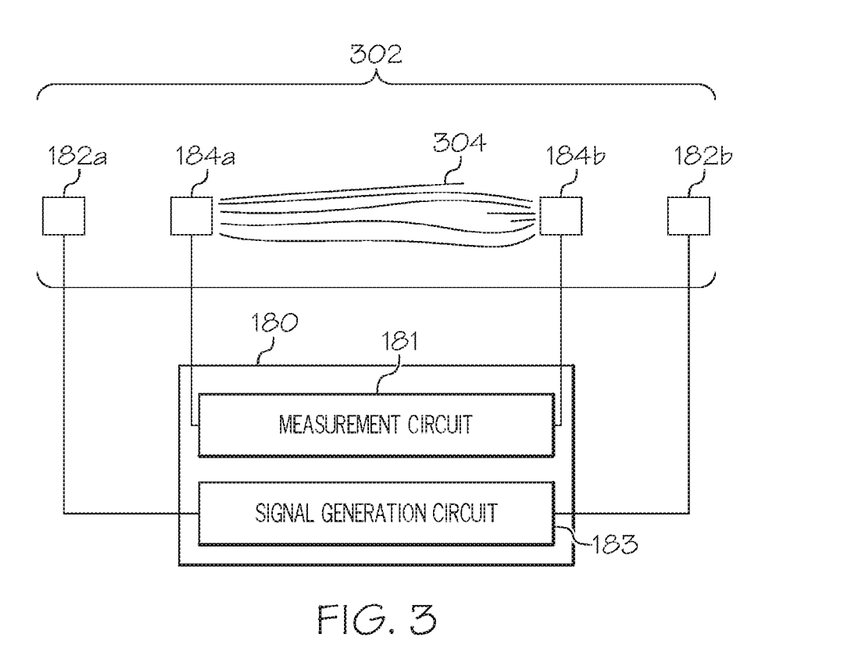
FIG. 3 schematically depicts a bladder muscle measurement unit with electrodes applied to a tissue region to measure a bladder muscle characteristic, according to one or more embodiments shown and described herein.

Referring now to FIG. 3, the bladder muscle measurement unit 180 is shown with electrodes coupled to a tissue region 302 in order to measure a bladder muscle activity parameter of a bladder muscle 304. The electrodes may be placed in a variety of locations of a patient. In some embodiments, such as what is depicted in FIG. 3, the electrodes may be applied to the skin of the patient at locations such that the bladder muscle 304 is disposed between the first bladder muscle electrical signal application electrode 182a and the second bladder muscle electrical signal application electrode 182b, and such that the bladder muscle 304 is disposed between the first bladder muscle measurement electrode 184a and the second bladder muscle measurement electrode 184b. A bladder muscle signal is received at the plurality of bladder muscle measurement electrodes 184a, 184b and processed by the measurement circuit 181 that is coupled to the plurality of bladder muscle measurement electrodes 184a, 184b. In some embodiments, the received bladder muscle signal is processed in order to determine a bladder muscle activity parameter, as will be described in further detail below.

Still referring to FIG. 3, in some embodiments, a second electrical output signal is generated with the signal generation circuit 183 and output with the plurality of bladder muscle electrical signal application electrodes 182a, 182b. The second electrical output signal may be an electrical signal of any type. For example, the second electrical output signal may be an alternating current signal having a constant peak-to-peak voltage, an alternating current signal having a constant current, an alternating current signal having a varying peak-to-peak voltage, an alternating current signal having a varying current, an alternating signal having a constant frequency, an alternating current signal having a varying frequency, a direct current signal having a constant voltage, a direct current signal having a constant current, a direct current signal having a varying voltage, a direct current signal having a varying current, or the like. The second electrical output signal may be a sine wave signal, a square wave signal, a triangular signal, or any other waveform. In embodiments that output the second electrical output signal, the bladder muscle signal may be received at the plurality of bladder muscle measurement electrodes

184a, 184b in response to the second electrical output signal. In some embodiments that output the second electrical output signal, the second electrical output signal may be an alternating current voltage signal having a second voltage and a second frequency. In some embodiments, the second frequency may be between 10 kHz and 100 kHz, though other embodiments may output signals having different frequencies.

Still referring to FIG. 3, the bladder muscle signal received at the plurality of bladder muscle measurement electrodes 184a, 184b may be processed to determine the bladder muscle activity parameter. In some embodiments, a bladder muscle signal parameter of the bladder muscle signal is measured. The bladder muscle signal parameter may be a voltage of the bladder muscle signal, a current of the bladder muscle signal, a standard deviation of the bladder muscle signal, a frequency of the bladder muscle signal, or any other signal parameter. For example, in some embodiments, the bladder muscle signal parameter is a bladder muscle signal current. A bladder muscle electrical impedance may be determined based on the bladder muscle signal current, such as by calculating the bladder muscle electrical impedance as a function of the bladder muscle signal current and one or more characteristics (e.g., voltage, frequency, etc.) of the second electrical output signal. The bladder muscle activity parameter may be determined based on the calculated or determined electrical impedance (e.g., based on a mapping or equation that determines the bladder muscle activity parameter from a calculated or determined bladder muscle electrical impedance). By way of another non-limiting example, in some embodiments, the bladder muscle signal parameter is a bladder muscle signal voltage. A bladder muscle electrical impedance may be determined based on the bladder muscle signal voltage, such as by calculating the bladder muscle electrical impedance as a function of the bladder muscle signal voltage and one or more characteristics (e.g., current) of the second electrical output signal. The bladder muscle activity parameter may be determined based on the calculated or determined bladder muscle electrical impedance (e.g., based on a mapping or equation that determines the bladder muscle activity parameter from a calculated or determined bladder muscle electrical impedance).

Still referring to FIG. 3, in some embodiments that output the second electrical output signal with the plurality of bladder muscle electrical signal application electrodes 182a, 182b, the second electrical output signal may be a constant current signal and the bladder muscle activity parameter may be determined based on a measured voltage of the bladder muscle signal received at the plurality of bladder muscle measurement electrodes 184a, 184b, such as by calculating an impedance based on the measured voltage, and determining the bladder muscle activity parameter based on the calculated impedance. In some embodiments that output the second electrical output signal with the plurality of bladder muscle electrical signal application electrodes 182a, 182b, the second electrical output signal may be a constant voltage signal and the bladder muscle activity parameter may be determined based on a measured current of the bladder muscle signal received at the plurality of bladder muscle measurement electrodes 184a, 184b, such as by calculating an impedance based on the measured current, and determining the bladder muscle activity parameter based on the calculated impedance. Some embodiments may calculate the bladder muscle activity parameter based on a standard deviation of the bladder muscle signal received at the plurality of bladder muscle measurement electrodes 184a, 184b, such as embodiments in which a high bladder muscle activity parameter is determined when the standard deviation is a first value and a low bladder muscle activity parameter is determined when the standard deviation is a second value that is less than the first value.

In some embodiments, electrical impedance myography (EIM) and/or electromyography (EMG) techniques may be employed by the bladder muscle measurement unit 180 in order to determine the bladder muscle activity parameter.

Figure 4:
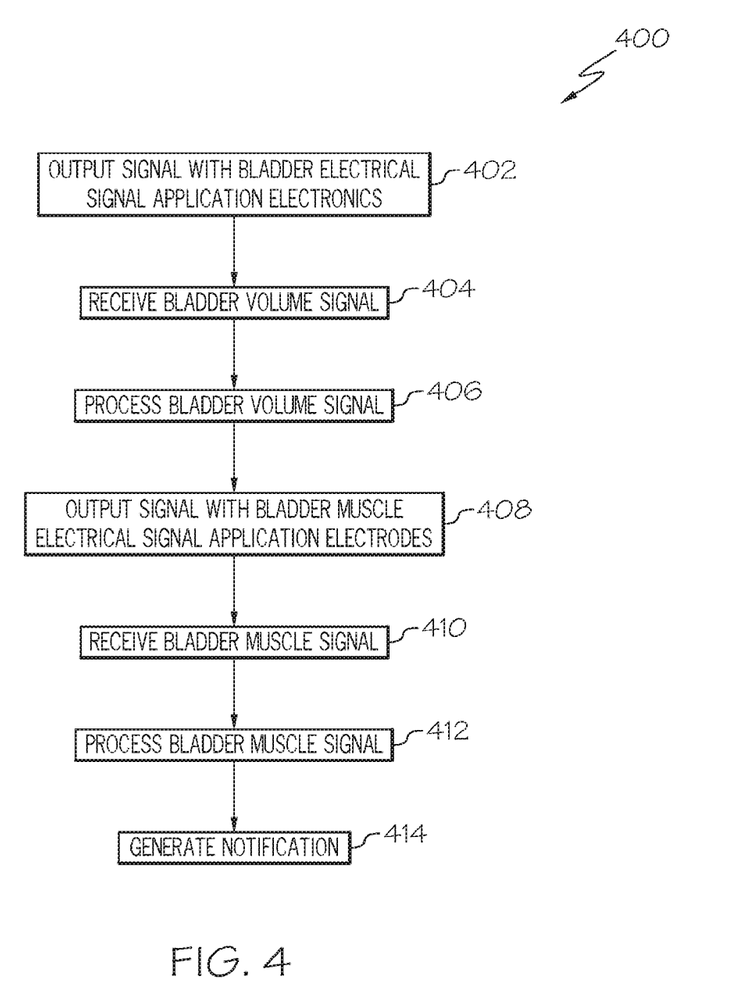
FIG. 4 schematically depicts a flowchart of a method for generating a notification based on a bladder volume signal and a bladder muscle signal, according to one or more embodiments shown and described herein.

Referring now to FIG. 4 in conjunction with FIGS. 1-3, a method 400 for generating a notification based on a bladder volume signal and a bladder muscle signal is schematically depicted. Although the steps associated with the blocks of FIG. 4 will be described as being separate tasks, in other embodiments, the blocks may be combined or omitted. Further, while the steps associated with the blocks of FIG. 4 will be described as being performed in a particular order, in other embodiments, the steps may be performed in a different order.

Still referring to FIG. 4, at block 402, the machine readable instructions stored in the one or more memory modules 132, when executed by the one or more processors 130, cause the system 100 to output a first electrical output signal with the plurality of bladder electrical signal application electrodes 172a, 172b. The first electrical output signal is generated by the signal generation circuit 173 and output between the first bladder electrical signal application electrode 172a and the second bladder electrical signal application electrode 172b. The first electrical output signal generated by the signal generation circuit 173 and output between the first bladder electrical signal application electrode 172a and the second bladder electrical signal application electrode 172b may be any type of electrical signal generated in any manner, including what is described above with reference to FIG. 2. Some embodiments may not output the first electrical output signal, such as embodiments that do not receive and process a bladder volume signal at the plurality of bladder volume measurement electrodes 174a, 174b in response to an output electrical signal.

Figure 5:
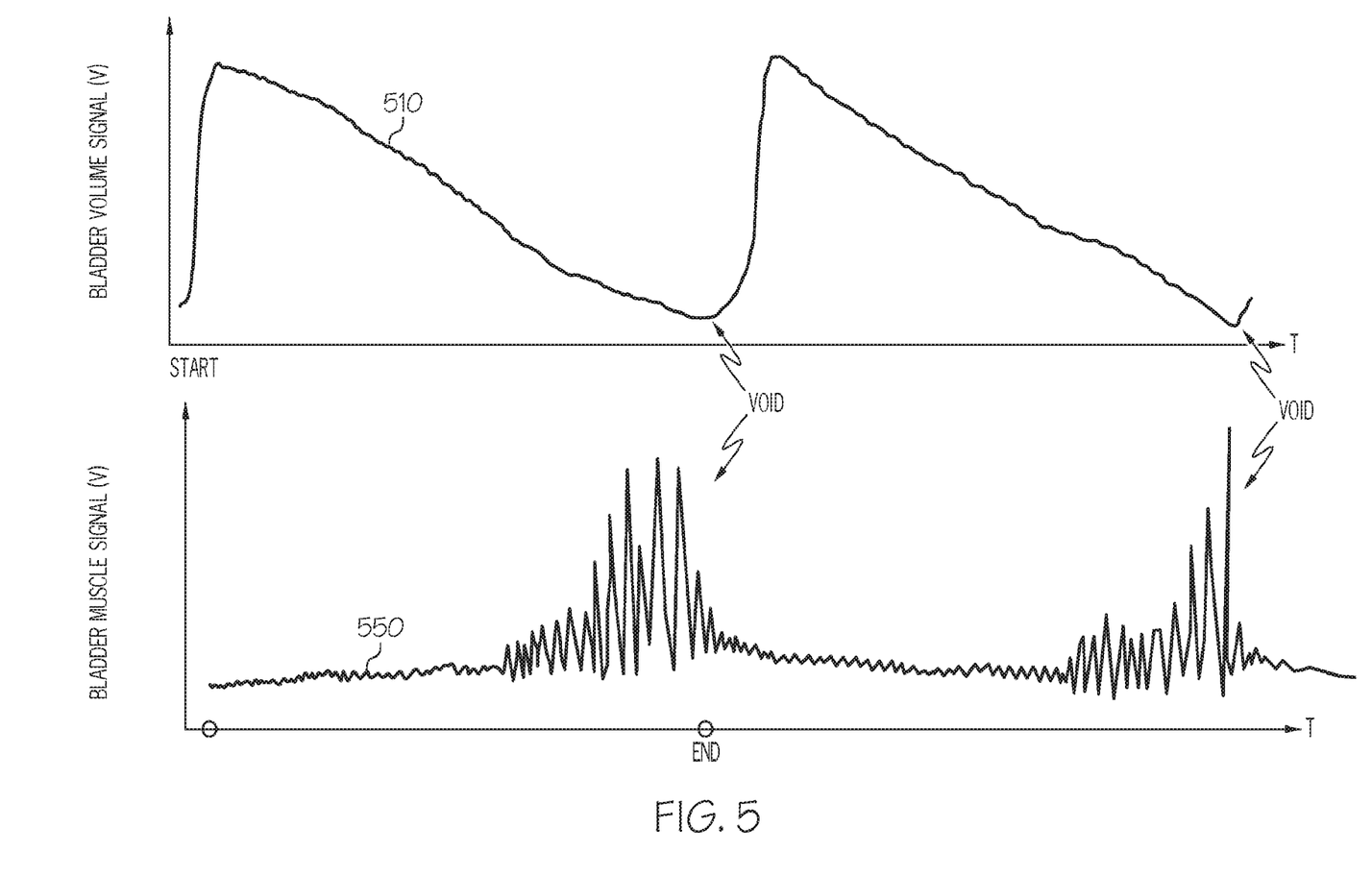
FIG. 5 schematically depicts a bladder volume signal waveform and a bladder muscle signal waveform, according to one or more embodiments shown and described herein.

Still referring to FIG. 4, at block 404, the machine readable instructions stored in the one or more memory modules 132, when executed by the one or more processors 130, cause the system 100 to receive a bladder volume signal at the plurality of bladder volume measurement electrodes 174a, 174b. In some embodiments, the bladder volume signal is received at the plurality of bladder volume measurement electrodes 174a, 174b in response to the first electrical output signal output between the plurality of bladder electrical signal application electrodes 172a, 172b at block 402. An example bladder volume signal 510 is shown in FIG. 5.

Referring once again to FIG. 4, at block 406, the machine readable instructions stored in the one or more memory modules 132, when executed by the one or more processors 130, cause the system 100 to process the bladder volume signal received at block 404. Processing the bladder volume signal may include filtering the bladder volume signal, determining a characteristic of the bladder volume signal, or measuring a bladder volume signal parameter of the bladder volume signal. A measured or determined bladder volume signal parameter may include a voltage of the bladder volume signal, a current of the bladder volume signal, a standard deviation of the bladder volume signal, a frequency of the bladder volume signal, or any other signal parameter. The bladder volume signal may be processed in any manner, including what is described above with reference to FIG. 2. In some embodiments, the bladder volume signal is processed by measuring a bladder volume signal parameter (e.g., a bladder volume signal voltage or bladder volume signal current), determining a bladder electrical impedance based on the measured bladder volume signal parameter (e.g., by calculating or determining the bladder electrical impedance based on the bladder volume signal voltage or the bladder volume signal current, as well as the signal parameters, such as voltage or current, of the first electrical output signal output by the plurality of bladder electrical signal application electrodes 172a, 172b in embodiments that output such a first electrical output signal), and determining the bladder volume based on the bladder electrical impedance (e.g., by using a bladder volume vs. bladder electrical impedance map or function).

In some embodiments that include processing the bladder volume signal to determine the bladder volume as described above, the machine readable instructions stored in the one or more memory modules 132, when executed by the one or more processors 130, cause the system 100 to determine a urine output parameter based on the bladder volume, such as by calculating a difference between the bladder volume at a previous time and the bladder volume determined based on the bladder volume signal at a current time. In some embodiments, the urine output parameter may be calculated as a difference between a maximum determined bladder volume determined at a first time and a minimum determined bladder volume determined at a second time. In some embodiments, the system 100 transmits the urine output parameter to the portable electronic device 190 and/or the remote computing device 192, such as to allow a nurse or caretaker to monitor the urine output of the patient.

Referring to FIG. 4, at block 408, the machine readable instructions stored in the one or more memory modules 132, when executed by the one or more processors 130, cause the system 100 to output a second electrical output signal with the plurality of bladder muscle electrical signal application electrodes 182a, 182b. The second electrical output signal is generated by the signal generation circuit 183 and output between the first bladder muscle electrical signal application electrode 182a and the second bladder muscle electrical signal application electrode 182b. The second electrical output signal generated by the signal generation circuit 183 and output between the first bladder muscle electrical signal application electrode 182a and the second bladder muscle electrical signal application electrode 182b may be any type of electrical signal generated in any manner, including what is described above with reference to FIG. 3. Some embodiments may not output the second electrical output signal, such as embodiments that do not receive and process a bladder muscle signal at the plurality of bladder muscle measurement electrodes 184a, 184b in response to an output electrical signal.

Still referring to FIG. 4, at block 410, the machine readable instructions stored in the one or more memory modules 132, when executed by the one or more processors 130, cause the system 100 to receive a bladder muscle signal at the plurality of bladder muscle measurement electrodes 184a, 184b. In some embodiments, the bladder muscle signal is received at the plurality of bladder muscle measurement electrodes 184a, 184b in response to the second electrical output signal output between the plurality of bladder muscle electrical signal application electrodes 182a, 182b at block 412. An example bladder muscle signal 550 is shown in FIG. 5.

Referring once again to FIG. 4, at block 412, the machine readable instructions stored in the one or more memory modules 132, when executed by the one or more processors 130, cause the system 100 to process the bladder muscle signal received at block 410. Processing the bladder muscle signal may include filtering the bladder muscle signal, determining a characteristic of the bladder muscle signal, or measuring a bladder muscle signal parameter of the bladder muscle signal. A measured or determined bladder muscle signal parameter may include a voltage of the bladder muscle signal, a current of the bladder muscle signal, a standard deviation of the bladder muscle signal, a frequency of the bladder muscle signal, or any other signal parameter. The bladder muscle signal may be processed in any manner, including what is described above with reference to FIG. 3. In some embodiments, the bladder muscle signal is processed by measuring a bladder muscle signal parameter (e.g., a bladder muscle signal standard deviation, a bladder muscle signal voltage, a bladder muscle signal current, etc.), determining a bladder muscle electrical impedance based on the measured bladder muscle signal parameter (e.g., by calculating or determining the bladder muscle electrical impedance based on the bladder muscle signal voltage or the bladder muscle signal current, as well as the signal parameters, such as voltage or current, of the second electrical output signal output by the plurality of bladder muscle electrical signal application electrodes 182a, 182b in embodiments that output such a second electrical output signal), and determining the bladder muscle activity parameter based on the bladder muscle electrical impedance (e.g., by using a bladder muscle activity parameter vs. bladder electrical impedance map or function). In some embodiments, the bladder muscle activity parameter is determined based on a standard deviation of the bladder muscle signal, such as described above.

Still referring to FIG. 4, at block 414, the machine readable instructions stored in the one or more memory modules 132, when executed by the one or more processors 130, cause the system 100 to generate a notification based on the bladder volume signal and the bladder muscle signal. The notification may be indicative of a predicted bed exit, a predicted need for a person to urinate, or the like. In some embodiments, the notification is generated based on a bladder volume signal parameter and a bladder muscle signal parameter, which may be measured or determined as described above. Some embodiments generate a notification by comparing a bladder volume signal parameter to a threshold and comparing a bladder muscle signal parameter to a threshold, and then generating the notification based on the comparisons. Some embodiments may compare a bladder volume signal voltage to a bladder volume signal voltage threshold and generate the notification based on the comparison. Some embodiments may compare a bladder volume signal current to a bladder volume signal current threshold and generate the notification based on the comparison. Some embodiments may compare a bladder muscle signal voltage to a bladder muscle signal voltage threshold and generate the notification based on the comparison. Some embodiments may compare a bladder muscle signal current to a bladder muscle signal current threshold and generate the notification based on the comparison. Some embodiments may compare a bladder muscle signal standard deviation to a bladder muscle signal standard deviation threshold and generate the notification based on the comparison.

Still referring to block 414 of FIG. 4, by way of non-limiting example, some embodiments may generate the notification when the bladder volume signal voltage is greater than a first threshold and the bladder muscle signal standard deviation is greater than a second threshold. By generating a notification indicative of a predicted bed exit, a predicted need for a person to urinate, or the like based on both of the bladder volume signal and the bladder muscle signal, reliability of the notification may be increased as compared to a system that utilizes only one of the bladder muscle signal and the bladder volume signal since a system that only utilizes one signal could result in the generation of false notifications. For example, patient movement may cause a spike in the bladder volume signal, which may result in the generation of a false notification if bladder volume signal alone were used to generate the notification. However, a system that utilizes both bladder volume signal and the bladder muscle signal to generate the notification may allow the system to filter out the spike in the bladder volume signal and avoid the generation of a false notification.

Still referring to block 414 of FIG. 4, in some embodiments that determine a bladder volume from the bladder volume signal as described above, the notification is generated based on the determined bladder volume. Some embodiments generate a notification by comparing a determined bladder volume to a bladder volume threshold and generate the notification based on the comparison as well as a comparison of a bladder muscle signal parameter to a threshold or a comparison of a value calculated from the bladder muscle signal to a threshold value. For example, some embodiments generate the notification when the determined bladder volume is greater than a threshold bladder volume and the standard deviation of the bladder muscle signal is greater than a threshold. Some embodiments generate a notification by comparing a difference between a determined bladder volume and a prior bladder volume (e.g., a predetermined bladder volume or a previously determined bladder volume) to a bladder volume difference threshold and generate the notification based on the comparison of the difference to the threshold as well as a comparison of a bladder muscle signal parameter to a threshold or a comparison of a value calculated from the bladder muscle signal to a threshold value. For example, some embodiments generate the notification when the determined bladder volume difference is greater than a threshold bladder volume difference and the standard deviation of the bladder muscle signal is greater than a threshold. Some embodiments may generate the notification based on a comparison of a determined bladder muscle activity parameter with a threshold.

Still referring to block 414 of FIG. 4, in some embodiments that determine a bladder electrical impedance from the bladder volume signal as described above, the notification is generated based on the determined bladder electrical impedance. Some embodiments generate a notification by comparing a determined bladder electrical impedance to a bladder electrical impedance threshold and generate the notification based on the comparison as well as a comparison of a bladder muscle signal parameter or value derived from a bladder muscle signal parameter to a threshold. For example, some embodiments generate the notification when the determined bladder electrical impedance is less than a threshold bladder electrical impedance and the standard deviation of the bladder muscle signal is greater than a threshold.

Some embodiments may calculate a confidence value based on the bladder volume signal and the bladder muscle signal, generate a first notification when the confidence value is less than a threshold, and generate a second notification when the confidence value is greater than the threshold. For example, when both the bladder volume signal and the bladder muscle signal indicates that the bladder may be full (e.g., when the bladder volume signal has a current or voltage associated with a high bladder volume and the bladder muscle signal has a high standard deviation associated with high bladder muscle activity corresponding to controlling a relatively full bladder), the confidence value may be determined to be a first value greater than the threshold. When the bladder volume signal and the bladder muscle signal disagree (e.g., when the bladder volume signal has a current or voltage associated with a high bladder volume and the bladder muscle signal has a low standard deviation associated with low bladder muscle activity corresponding to a relaxed state), the confidence value may be determined to be a second value that is less than the first value and less than the threshold. In such a case where the bladder volume signal and the bladder muscle signal disagree, using only one of the signals alone is less reliable and using both signals together increases reliability of a predicted bed exit or predicted need for a person to urinate. For example, patient movement may cause a spike in the bladder volume signal that is not associated with a full bladder, and utilizing the bladder muscle signal as a secondary channel may allow the system to confidently determine whether a bed exit can be reliably predicted. In some embodiments, the first notification generated when the confidence value is less than a threshold may be a simple alert or prompt issued to the patient (e.g. with the one or more speakers 140 and/or the one or more displays 134). Once alerted or prompted, the patient may then request that a caregiver or nurse be alerted so that the caregiver or nurse may take the patient to the restroom if necessary, thereby mitigating the risk of a fall or injury. The patient may request that the caregiver or nurse be alerted by providing input to the system 100 via the tactile input hardware 138 (e.g., by manipulating a "call" button or the like), via the one or more microphones 142 (e.g., by issuing a voice command to the system), or in any other manner. In some embodiments, the second notification generated when the confidence value is greater than the threshold may be a notification to a caregiver or nurse, which may be transmitted from the system 100 with the network interface hardware 146, received by the portable electronic device 190 and/or the remote computing device 192, which provides the notification to the caregiver or nurse via one or more speakers or display devices of the portable electronic device 190 and/or the remote computing device 192. Once the caregiver or nurse is alerted, the caregiver or nurse can check on the patient and take the patient to the restroom if necessary, thereby mitigating the risk of a fall or injury. In some embodiments, the notification may be generated in response to determining that a patient may need to urinate within a predetermined amount of time, such as within 90 seconds, within 10 minutes, or the like.

The various thresholds described above for determining when to generate a notification indicative of a predicted bed exit arising from an individual having an urge to urinate varies among people and among circumstances. Some embodiments may set one or more thresholds used for generating notifications by monitoring conditions and parameters during a plurality of bladder fill and void cycles. For example, when bladder electrical impedance is used to generate the notification, a threshold bladder electrical impedance may be determined by monitoring a minimum bladder electrical impedance among a plurality of bladder fill and void cycles and then determining a threshold bladder electrical impedance based on the minimum bladder electrical impedances among the plurality of bladder fill and void cycles, such as by averaging the minimum bladder electrical impedances. The threshold bladder electrical impedance may be representative of a holding capacity of an individual's bladder and may be used to generate notifications indicative of a predictive need for the individual to urinate (e.g., by comparing a calculated bladder electrical impedance at a current time to the threshold bladder electrical impedance and generating the notification based, at least in part, on determining that the calculated bladder electrical impedance is less than the threshold bladder electrical impedance or differs from the threshold bladder electrical impedance by less than a threshold amount). By way of another example, when bladder volume signal voltage is used to generate the notification, a threshold bladder volume signal voltage may be determined by monitoring a maximum bladder volume signal voltage among a plurality of bladder fill and void cycles and then determining a threshold bladder volume voltage based on the maximum bladder volume signal voltages among the plurality of bladder fill and void cycles, such as by averaging the maximum bladder volume signal voltages. The threshold bladder volume signal voltage may be representative of a holding capacity of an individual's bladder and may be used to generate notifications indicative of a predictive need for the individual to urinate (e.g., by comparing a bladder volume signal voltage measured at a current time to the threshold bladder volume signal voltage and generating the notification based, at least in part, on determining that the measured bladder volume signal voltage is greater than the threshold bladder volume signal voltage or differs from the threshold bladder volume signal voltage by less than a threshold amount).

In some embodiments, the thresholds for generating the notifications may be determined differently. For example, a first electrical output signal may be output with the plurality of bladder electrical signal application electrodes 172a, 172b and a bladder volume signal may be received at the plurality of bladder volume measurement electrodes in response to the first electrical output signal in the manner described above. A first bladder void event may be determined based on the received bladder volume signal (such as by determining when a bladder volume signal voltage is at a first local minimum, as shown by the void event indicated in the middle of the graphs shown in FIG. 5). A first bladder void parameter associated with the first bladder void event may be determined based on the bladder volume signal. For example, the first bladder void parameter may be a first voltage of the bladder volume signal associated with the first bladder void event. A second bladder void event may be determined based on the received bladder volume signal (such as by determining when a bladder volume signal voltage is at a second local minimum, as shown by the void event indicated on the right side of the graphs shown in FIG. 5). A second bladder void parameter associated with the second bladder void event may be determined based on the bladder volume signal. For example, the second bladder void parameter may be a second voltage of the bladder volume signal associated with the second bladder void event. A first bladder void parameter threshold may be determined based on the first bladder void parameter and the second bladder void parameter. For example, the first bladder void parameter threshold may be a first voltage threshold that is determined based on the first voltage of the bladder volume signal and the second voltage of the bladder volume signal, such as by averaging the first voltage and the second voltage. The first bladder void parameter threshold may then be used to generate a notification based on the bladder volume signal at a current time. For example, a first current bladder void parameter may be determined based on the bladder volume signal at the current time, the first current bladder void parameter may be compared to the first bladder void parameter threshold, and a notification may be generated based on the comparison. Carrying through the same non-limiting example, a current bladder volume signal voltage may be determined, the current bladder volume signal voltage may be compared to the first voltage threshold, and a notification may be generated based on the comparison, such as when the current bladder volume signal voltage exceeds the first voltage threshold or a difference between the first voltage threshold and the current bladder volume signal voltage is less than a threshold amount.

Some embodiments may also use bladder muscle signal information to determine the thresholds. For example, some embodiments receive a bladder muscle signal at the plurality of bladder muscle measurement electrodes 184a, 184b, determine the first bladder void event based on the received bladder volume signal and the received bladder muscle signal (e.g., by determining when a bladder volume signal voltage is at a first local minimum and a bladder muscle signal standard deviation is above a threshold amount at a first time), and determine the second bladder void event based on the received bladder volume signal and the received bladder muscle signal (e.g., by determining when a bladder volume signal voltage is at a second local minimum and a bladder muscle signal standard deviation is above a threshold amount at a second time after the first time).

Still referring to block 414 of FIG. 4, some embodiments may generate the notification based on additional inputs other than the bladder volume signal and the bladder muscle signal. For example, some embodiments receive an inertial measurement signal from the one or more inertial measurement units 136 and generate the notification based on the bladder volume signal, the bladder muscle signal, and the inertial measurement signal. At least one of the one or more inertial measurement units 136 may be coupled to a body of the patient such that the one or more inertial measurement units 136 outputs an inertial measurement signal indicative of a movement of the patient. For example, some embodiments may detect a high degree of movement based on the inertial measurement signal and generate the notification based on the detected high degree of movement, which may indicate that a person is uncomfortable and needs to utilize the restroom. Some embodiments may use an inertial measurement signal output by the one or more inertial measurement units 136 to detect a potential false positive in the bladder volume signal, which have been caused by a change in the patient's orientation or posture, further increasing the reliability of the notification.

Still referring to block 414 of FIG. 4, some embodiments receive image data from the one or more cameras 144 and generate the notification based on the bladder volume signal, the bladder muscle signal, and the image data. The one or more cameras 144 are positioned such that a patient is within the field of view of the one or more cameras 144. For example, some embodiments may detect a high degree of movement based on analyzing the image data and generate the notification based on the detected high degree of movement, which may indicate that a person is uncomfortable and needs to utilize the restroom.

Some embodiments transmit the notification generated at block 414 to the portable electronic device 190 and/or to the remote computing device 192, each of which may generate an appropriate alert or notification to a caregiver or nurse indicative of a predicted bed exit or that an individual may need to take a trip to the restroom. By generating such a notification, the need to use the restroom may be predicted early enough so that a caregiver may assist a person to the restroom before the person attempts to use the restroom himself or herself, which may create an undesirable risk of a fall or injury.

It should be understood that embodiments described herein are directed to systems and methods for generating notifications based on bladder volume signals and bladder muscle signals. The system outputs a first electrical output signal with a plurality of bladder electrical signal application electrodes, receives a bladder volume signal at a plurality of bladder volume measurement electrodes in response to the first electrical output signal, receives a bladder muscle signal at a plurality of bladder muscle measurement electrodes, and generates a notification based on the bladder volume signal and the bladder muscle signal. By generating a notification (e.g., a notification indicative of a predicted bed exit, a predicted need for a person to urinate, or the like) based on both of the bladder volume signal and the bladder muscle signal, reliability of the notification may be increased as compared to a system that utilizes only one of the bladder muscle signal and the bladder volume signal since a system that only utilizes one signal could result in the generation of false notifications.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A system for generating a notification based on a bladder volume signal and a bladder muscle signal, the system comprising:
   a processor;
   a plurality of bladder electrical signal application electrodes communicatively coupled to the processor;
   a plurality of bladder volume measurement electrodes communicatively coupled to the processor;
   a plurality of bladder muscle measurement electrodes communicatively coupled to the processor;
   a plurality of bladder muscle electrical signal application electrodes communicatively coupled to the processor;
   a memory module communicatively coupled to the processor; and
   machine readable instructions stored in the memory module that cause the system to perform at least the following when executed by the processor:
      output a first electrical output signal with the plurality of bladder electrical signal application electrodes;
      receive the bladder volume signal at the plurality of bladder volume measurement electrodes in response to the first electrical output signal;
      output a second electrical output signal with the plurality of bladder muscle electrical signal application electrodes;
      receive the bladder muscle signal at the plurality of bladder muscle measurement electrodes in response to the second electrical output signal;
      measure a bladder volume signal parameter of the bladder volume signal received at the plurality of bladder volume measurement electrodes in response to the first electrical output signal;
      measure a standard deviation of the bladder muscle signals received at the plurality of bladder muscle measurement electrodes;
      compare the bladder volume signal parameter to a bladder volume signal threshold;
      compare the standard deviation to a bladder muscle signal threshold; and
      generate the notification related to impending urination in response to the bladder volume signal parameter being greater than the bladder volume signal threshold and the standard deviation being greater than the bladder muscle signal threshold.

2. The system of claim 1, wherein:
   the second electrical output signal is an alternating current voltage signal having a voltage and a frequency;
   the bladder muscle signal is a bladder muscle signal current,
   wherein, when executed by the processor, the machine readable instructions further cause the system to:
   determine a bladder muscle electrical impedance based on the bladder muscle signal current;
   determine a bladder muscle activity parameter based on a standard deviation of the bladder muscle electrical impedance; and
   generate the notification based on the bladder muscle activity parameter.

3. The system of claim 1, wherein:
   the second electrical output signal has a current;
   the bladder muscle signal is a bladder muscle signal voltage,
   wherein, when executed by the processor, the machine readable instructions further cause the system to:
   determine a bladder muscle electrical impedance based on the bladder muscle signal voltage;
   determine a bladder muscle activity parameter based on a standard deviation of the bladder muscle electrical impedance; and
   generate the notification based on the bladder muscle activity parameter.

4. The system of claim 1, wherein:
   the first electrical output signal is an alternating current voltage signal having a first voltage and a first frequency;
   the bladder volume signal parameter is a bladder volume signal current,
   wherein, when executed by the processor, the machine readable instructions further cause the system to:
   determine a bladder electrical impedance based on the bladder volume signal current;
   determine a bladder volume based on the bladder electrical impedance; and
   generate the notification based on the bladder volume.

5. The system of claim 4, wherein the first frequency is between 10 kHz and 100 kHz.

6. The system of claim 1, wherein:
   the first electrical output signal has a first current;
   the bladder volume signal parameter is a bladder volume signal voltage,
   wherein, when executed by the processor, the machine readable instructions further cause the system to:

determine a bladder electrical impedance based on the bladder volume signal voltage;

determine a bladder volume based on the bladder electrical impedance; and generate the notification based on the bladder volume.

7. The system of claim 1, further comprising an inertial measurement unit communicatively coupled to the processor, wherein when executed by the processor the machine readable instructions further cause the system to:

receive an inertial measurement signal from the inertial measurement unit; and generate the notification based on the bladder volume signal, the bladder muscle signal, and the inertial measurement signal.

8. The system of claim 1, further comprising a camera communicatively coupled to the processor, wherein when executed by the processor the machine readable instructions further cause the system to:

receive image data from the camera; and generate the notification based on the bladder volume signal, the bladder muscle signal, and the image data.

9. The system of claim 1, further comprising network interface hardware communicatively coupled to the processor, wherein the machine readable instructions, when executed by the processor, further cause the system to transmit the notification to a portable electronic device with the network interface hardware.

10. The system of claim 9, wherein the machine readable instructions, when executed by the processor, further cause the system to:

determine a bladder volume based on the bladder volume signal;

determine a urine output parameter based on the bladder volume; and transmit the urine output parameter to the portable electronic device.

11. The system of claim 1, wherein the machine readable instructions, when executed by the processor, further cause the system to:

calculate a confidence value based on the bladder volume signal and the bladder muscle signal;

generate a first notification when the confidence value is less than a threshold; and generate a second notification when the confidence value is greater than the threshold, wherein the first notification and the second notification are different.

12. The system of claim 1, wherein the machine readable instructions stored in the memory module that cause the system to perform at least the following when executed by the processor:

determine an occurrence of a first bladder void event based on the received bladder volume signal;

determine a first bladder void parameter associated with the first bladder void event, wherein the first bladder void parameter is determined based on the bladder volume signal;

determine an occurrence of a second bladder void event based on the received bladder volume signal;

determine a second bladder void parameter associated with the second bladder void event, wherein the second bladder void parameter is determined based on the bladder volume signal;

determine a first bladder void parameter threshold based on the first bladder void parameter and the second bladder void parameter;

determine a first current bladder void parameter based on the bladder volume signal;

compare the first current bladder void parameter to the first bladder void parameter threshold; and generate a notification based on the comparison of the first current bladder void parameter and the first bladder void parameter threshold.

13. The system of claim 12, wherein the first bladder void parameter threshold is representative of a holding capacity of an individual's bladder.

14. The system of claim 12, wherein the machine readable instructions, when executed by the processor, further cause the system to:

determine the first bladder void parameter threshold by averaging the first bladder void parameter and the second bladder void parameter.

* * * * *